United States Patent [19] [11] 4,241,222
MacLeay [45] Dec. 23, 1980

[54] PROCESS FOR THE PREPARATION OF CUMYL PEROXIDES

[75] Inventor: Ronald E. MacLeay, Williamsville, N.Y.

[73] Assignee: Pennwalt Corporation, Philadelphia, Pa.

[21] Appl. No.: 75,355

[22] Filed: Sep. 13, 1979

[51] Int. Cl.$^3$ .............................................. C07C 179/06
[52] U.S. Cl. .................................................... 568/561
[58] Field of Search ........................ 568/558, 560, 561

[56] References Cited

U.S. PATENT DOCUMENTS

| 3,267,066 | 8/1966 | Tijssen | 568/558 |
| 3,829,503 | 8/1974 | Kato et al. | 568/558 |
| 4,133,835 | 1/1979 | Bafford et al. | 568/558 |

FOREIGN PATENT DOCUMENTS

| 1046054 | 12/1956 | Fed. Rep. of Germany | 568/558 |
| 1216305 | 12/1966 | Fed. Rep. of Germany | 568/561 |
| 2035127 | 6/1973 | Fed. Rep. of Germany | 568/561 |
| 961481 | 6/1964 | United Kingdom | 568/561 |

OTHER PUBLICATIONS

Chem. Abs. vol. 82, (1975), p. 125098n.

Primary Examiner—Werren B. Lone

[57] ABSTRACT

An aliphatic or cycloaliphatic hydroperoxide or aliphatic dihydroperoxide, an olefin such as alpha-methylstyrene or a substituted alpha-methylstyrene wherein the substituent is on the phenyl ring and a t-cumyl halide corresponding to the hydrohalogenated olefin such as t-cumyl chloride or a substituted t-cumyl chloride are reacted under relatively non-aqueous conditions, in the absence of a free acid and in the presence of a phenol catalyst, to obtain a cumyl (or substituted cumyl) peroxide or diperoxide corresponding to the hydroperoxide or dihydroperoxide. The cumyl peroxides prepared by this reaction are very useful as crosslinking agents for polyethylene and elastomers.

6 Claims, No Drawings

PROCESS FOR THE PREPARATION OF CUMYL PEROXIDES

BACKGROUND OF THE DISCLOSURE

1. Field of the Invention

This invention relates to an improved process for the preparation of cumyl peroxides or cumyl diperoxides. More particularly, the invention relates to an improvement in the process of preparing cumyl peroxides by reacting an aliphatic or cycloaliphatic hydroperoxide or aliphatic dihydroperoxide, an olefin and a cumyl halide corresponding to the olefin under non aqueous conditions in the absence of a free acid and in the presence of a phenol catalyst.

2. Description of the Prior Art

The preparation of aralkyl and alkyl peroxides is well known in the prior art and can best be summarized under four major methods of preparation:

(1) The acid-catalyzed condensation of a hydroperoxide with an alcohol.
(2) The acid-catalyzed addition of a hydroperoxide to an olefin.
(3) The displacement reaction between an alkali metal salt of a hydroperoxide and an alkyl halide.
(4) The displacement reaction between a hydroperoxide or hydrogen peroxide and an alkyl halide in the presence of an acid acceptor.

The fourth method is the only method relevant to this invention. The other methods and their short-comings in the preparation of cumyl peroxide are thoroughly discussed in U.S. Pat. No. 4,133,835 (Bafford). This invention is essentially an improvement over Bafford's process as taught in U.S. Pat. No. 4,133,835. Prior art pertaining to the fourth method above is: Kato et. al. (Auslegeschrift No. 2,035,127) published a process for preparing t-cumyl type peroxides by reacting a tertiary hydroperoxide with an aralkyl halide, such as t-cumyl chloride, at 0°–80° C. in the presence of an acid binding agent such as a t-alcohol or an aliphatic olefin. The mole ratio of the aralkyl halide to the hydroperoxide could vary from 1:1 to 1:1.5. In this process the hydroperoxide reacts with the aralkyl halide to form the peroxide; the HCl generated is taken up by the acid binding agent. There is no regeneration of the t-cumyl chloride. Kato's process was run with an acid sensitive aralkyl hydroperoxide, cumene hydroperoxide, with t-cumyl chloride in the presence of t-butyl alcohol (see Example XX). Although the reaction ran quite fast, only a 36% yield of dicumyl peroxide was obtained. There was a considerable amount of phenol generated during the reaction indicating the t-butyl alcohol was not a good scavenger of the hydrogen chloride; consequently a large amount of the cumene hydroperoxide underwent acid catalyzed decomposition to form phenol and acetone.

Kloosterman et al. (Auslegeschrift No. 1,216,305) describes a process for the preparation of dicumyl peroxide and its ring chlorinated derivatives by the reaction of t-cumyl chloride or its ring chlorinated derivatives with an aqueous solution of hydrogen peroxide at 0°–40° C. in the presence of an acid binding medium so that the pH of the reaction mixture stays between −1 and 2.5 on a glass/Kalomel electrode. In a stronger acid medium, decomposition exotherms were reported to occur. A mole ratio of t-cumyl chloride to hydrogen peroxide of 1:0.5 to 1:0.8 were used in this system. The anhydrous basic acid binding agents, such as $Na_2CO_3$, $K_2CO_3$ or $NH_3$, had to be added portionwise throughout the reaction so that the pH held between −1 and 2.5.

Bafford's (U.S. Pat. No. 4,133,835) process consisted of adding an aliphatic or cycloaliphatic hydroperoxide to an olefin such as a 1-aromatic-1-substituted ethylene and a halide corresponding to the ethylene under essentially anhydrous conditions in the absence of a free acid, at a temperature below the decomposition temperature of the halide. The main object of this invention was to provide a process for the preparation of certain peroxides, especially acid-sensitive peroxides by a procedure that does not use a free-acid catalyst. The process is similar to that of Kato's except Bafford uses the 1-aromatic-1-substituted ethylene as the acid binding agent. By doing this aralkyl halide is regenerated. Consquently, a low concentration of the aralkyl halide in the olefin can be used; the reaction becomes less acid sensitive and the economics are much better. Bafford stresses the importance of having an excess of hydroperoxide over the olefin/aralkyl halide.

None of the prior art teaches the use of phenols as catalysts; to the best of our knowledge there never has been any mention in the literature of using phenols as catalysts for making peroxides.

STATEMENT OF THE INVENTION

This invention is directed to an improvement in the process of preparing the cumyl peroxides comprising reacting an aliphatic or cycloaliphatic hydroperoxide or aliphatic dihydroperoxide, an olefin such as alpha-methylstyrene or a substituted alpha-methylstyrene, and a t-cumyl halide corresponding to the hydrohalogenated olefin such as t-cumyl chloride (or bromide) or a substituted t-cumyl chloride (or bromide) in the presence of a phenol catalyst under relatively non-aqueous conditions to form a cumyl (or substituted cumyl) peroxide or diperoxide corresponding to the hydroperoxide or dihydroperoxide.

DETAILED DESCRIPTION OF THE INVENTION

The olefin is alpha-methylstyrene or a substituted alpha-methylstyrene of Formula I

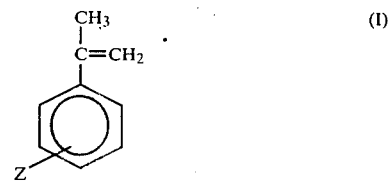

where the substituent Z is an inert group substituted on the phenyl ring of the alpha-methylstyrene. Suitable substituents include hydrogen, lower alkyl groups of 1 to 6 carbons such as methyl, ethyl, propyl, isopropyl, butyl, t-butyl, amyl, t-amyl or hexyl, halo groups such as chloro, bromo or fluoro, ether groups such as methoxy, ethoxy, propoxy, isopropoxy or phenoxy and aryl groups such as phenyl or naphthyl.

The reactive halide is t-cumyl chloride or bromide or a substituted t-cumyl chloride or bromide of Formula II

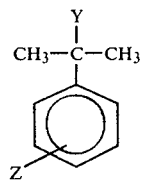

where the substituent Z is an inert group substituted on the phenyl ring of the t-cumyl halide, Y is chlorine or bromine and the reactive halide is the addition product of hydrogen chloride or hydrogen bromide to the particular olefin employed.

The organic hydroperoxide is an aliphatic or cycloaliphatic hydroperoxide or aliphatic dihydroperoxide having the general formula III

where y is 1 or 2;
when y is 1, R is selected from lower t-alkyl of 4 to 8 carbons, lower t-alkynyl of 5 to 8 carbons, t-aralkyl of 9 to 12 carbons or t-cycloalkyl of 6 to 10 carbons; and when y is 2, R is selected from

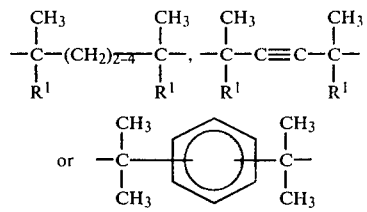

where $R^1$ is an alkyl of 1 to 6 carbons.

Suitable hydroperoxides include t-butyl hydroperoxide, t-amyl hydroperoxide, t-hexyl hydroperoxide, 1,1,3,3-tetramethylbutyl hydroperoxide, cumene hydroperoxide, cymene hydroperoxide, p-menthane hydroperoxide, 1-methylcyclohexyl hydroperoxide, 1-methylcyclopentyl hydroperoxide, 3-hydroperoxy-3-methylbutyne-1,2-hydroperoxy-2-methyl-4-hydroxypentane and 1-hydroperoxycyclohexylacetylene. Suitable dihydroperoxides include 2,5-dimethyl-2,5-dihydroperoxyhexane, 2,7-dimethyl-2,7-dihydroperoxyoctane, 2,5-dimethyl-2,5-dihydroperoxyhexyne-3 and diisopropylbenzene dihydroperoxides.

The phenyl catalyst is phenol, naphthol or a substituted phenol or naphthol of Formula IV or V,

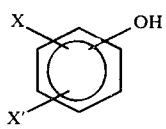 or 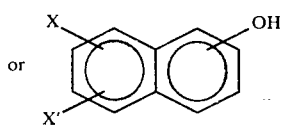

(IV)                  (V)

with inert substituents X and X' which may be the same or different but when neither is hydrogen both X and X' cannot be substituted ortho to the hydroxyl group at the same time. X and X' are selected from hydrogen, lower alkyl groups of 1 to 6 carbons, lower alkoxy groups of 1 to 6 carbons, aryloxy groups of 6 to 10 carbons, also groups such as chloro, bromo, fluoro or aryl groups of 6 to 10 carbons. It should be understood that when X and X' are hydrogen atoms, the phenol or naphthol are unsubstituted. Preferably the substituents should not be in the position ortho to the OH group where they would create steric hindrance to the OH group. For example, the hydroxyl group in 2,6-diisopropylphenol is too sterically hindered to generate any catalytic effect on the reaction. o-Cresol is not as effective as p-cresol.

The following is a list of suitable phenols and naphthols: phenol, ortho, meta and para cresols, chlorophenols, bromophenols, methoxyphenols, ethylphenols, isopropylphenols, para-t-butylphenol, paraphenylphenol, 3,4-dichlorophenol, 3,4-dimethylphenol, alpha-naphthol and beta-naphthol.

From a practical standpoint it is advantageous to use a cheap low molecular weight phenol which can be readily extracted out of the reaction mixture with aqueous caustic. Phenol and the meta and para cresols or mixtures thereof are especially suitable. alpha- and beta-Naphthols are also suitable.

The reaction is run in the temperature range of 10°–50° C. preferably 15°–45° C. Since the phenol acts as a catalyst, the reaction temperature and reaction time are quite dependent on the amount of phenol added. When small amounts of phenol are added, the reaction will take longer and should be run at a higher temperature than when larger amounts of phenol are added. In practice we have found that it is advisable to start the reaction out at a low temperature, 15°–25° C., while the bulk of the reaction is going on and then program the reaction temperature up as the reaction slows down. In most cases the reaction can be monitored by gas chromatography.

The mole ratio of olefin groups to hydroperoxide groups can vary from 0.5:1 to 5:1. The yield of peroxide based on the hydroperoxide increases as the mole ratio of olefin to hydroperoxide increases from 1:1 to 2:1. Increasing the mole ratio of olefin to hydroperoxide above 2:1 does not improve the yield and would only be applied when there is a problem of solubility of the hydroperoxide in the reaction system. In practice a mole ratio of approximately 1.3:1 is optimum in regards to yields and the amount of product that can be made per given reactor volume. Although one could run the reaction at a mole ratio less than 1:1, in most cases it would not be economically advisable.

The t-cumyl halide is charged in an amount of about 5–20 mole percent based on the olefin charged. Generally one would use 7–12 mole percent. Increasing the mole percent t-cumyl halide increases the reaction rate but usually increases the amount of impurities generated as well.

The components of the feed may be charged to the reaction zone in any order; but it has been found preferable to add the t-cumyl halide to a solution of the hydroperoxide, olefin and phenol or to add a solution of the phenol in the hydroperoxide to the solution of t-cumyl halide in the alpha-methylstyrene or add the phenol last since a mixture of the olefin, t-cumyl halide and phenol, in the absence of hydroperoxide, undergoes some degree of oligomerization of the olefin. When the t-cumyl halide is added last, the t-cumyl halide can be added neat or as a solution in the olefin or even in an inert diluent. The addition of the t-cumyl halide should be carried out at such a rate and temperature that the reaction can be easily controlled. If the halide is added too fast at a high temperature in the presence of a considerable amount of phenol, a runaway reaction could occur.

The system does not have to be completely anhydrous but water does have a rate retarding effect. It has been found beneficial in some cases, from an ease in handling standpoint, to use liquified phenol which contains about 9% water. When using liquified phenol you have to increase the amount of phenol used by about 10% to override the rate retarding effect of the water.

For each peroxide, the mole ratios, temperature, addition rate and phenol level have to be adjusted slightly to obtain the optimum results. The cumyl peroxide compounds produced in process of this invention are useful crosslinking agents for high and low density polyethylene, elastomers and rubbers.

EXAMPLES

The examples will demonstrate the preparation of various cumyl peroxides using the phenol catalyzed system, the effect of the phenol on the time required to complete the reaction and the advantages of the phenol catalyzed system over the prior art systems. They will also demonstrate that various phenols are effective catalysts and that alcohols, ketones and organic acids are not.

Most reactions were monitored by gas chromatography (G.C. or VPC) and the values given in the example tables will be area percentage values obtained by integration of the VPC scans. Although these values are not absolute [a small percentage (~2%) of material does not come through the VPC], they are relative and will clearly demonstrate the catalytic effect of the phenol. The gas chromatographic analyses were carried out on a Hewlett Packard 5710A gas chromatograph coupled to a 3380S integrator. An 18 inch ⅛ inch diameter 3% OV-17 column was used. The injection port temperature was 110° C. and the thermal detector temperature was 250° C. For dicumyl peroxide the temperature was programmed at 8° C. per minute from 45° C. to 210° C. and the helium flow rate was approximately 90 cc per minute. The dicumyl peroxide was diluted about 6:1 in pentane to flush it through the injection point. A 0.25 minute delay was carried on the integrator so the pentane would not integrate. The temperature program rate and helium flow were cut back for the more volatile peroxides.

Final assays and yields in most cases were determined accurately by liquid chromatography using analytically pure standards and internal standards.

EXAMPLE I

Preparation of t-Cumyl Chloride

Into a jacketed 2 liter reactor equipped with a thermometer, gas inlet tube, mechanical stirrer, bottom outlet and a water-cooled condenser connected to a gas bubbler was added 708 grams (6 moles) of alpha-methylstyrene. Hydrogen chloride was passed into the alpha-methylstyrene over 2½ hours at 27°–29° C. at a slow enough rate that complete absorption was obtained. After 226.3 grams (6.2 moles) of hydrogen chloride had been added, absorption ceased and the hydrogen chloride bubbled through the gas bubbler. The addition was stopped and the solution was stirred ½ hour at 28°–29° C. The product was drained into a tared glass bottle and weighed. The bottle was tightly capped and stored in the freezer compartment of a refrigerator. The product weighed 927 grams for a 100% yield. The product was used as a stock solution for the subsequent reactions.

Although it is more practical on a commercial basis to prepare a solution of cumyl chloride in alpha-methylstyrene, it was found much easier on a laboratory scale to make the solution by adding a weighed amount of 100% t-cumyl chloride to a predetermined amount of alpha-methylstyrene. It was much easier to obtain accurate concentrations of the t-cumyl chloride in the alpha-methylstyrene operating in this manner rather than trying to accurately weigh small amounts of hydrogen chloride into the alpha-methylstyrene each time.

EXAMPLE II

Preparation of Dicumyl Peroxide

This example demonstrates the difference between a phenol catalyzed reaction and a noncatalyzed reaction in the preparation of dicumyl peroxide. The reactions were monitored by gas chromatography.

A. Phenol Catalyzed Reaction

Six grams (0.064 m) of phenol were dissolved in 57.4 grams (0.315 m) of 83.5% cumene hydroperoxide by stirring the solid phenol in a beaker with the cumene hydroperoxide with a magnetic stirrer at room temperature.

Into a 200 ml jacketed reactor equipped with a mechanical stirrer, thermometer, water-cooled condenser and addition funnel were added 47.2 grams (0.4 m) alpha-methylstyrene and 6.7 grams (0.043 m) t-cumyl chloride. The stirrer was activated and the temperature of the solution was adjusted to 15° C. by circulating cold water through the reactor jacket. The cumene hydroperoxide solution was transferred to the addition funnel and added to the reactor over 8 minutes at 15° C. The reaction was stirred an additional 5 minutes at 15° C.; then the reaction was warmed to 30° C. over 5 minutes and stirred 25 minutes at 30° C., and 1¼ hours at 45° C. at which point the cumene hydroperoxide was completely consumed. The reaction was terminated by adding 50 mls of water, stirring 15 minutes, adding 10 mls of 50% NaOH, stirring an additional 15 minutes and separating the aqueous caustic layer. The organic layer was successively washed with 50 ml portions of water, 15% NaHSO₃ solution, water, saturated NaHCO₃ solution, ½% HCl and water. The volatiles were steam distilled out of the crude product under vacuum (See Example III). The organic residue after isolation and drying weighed 61.5 grams and assayed 96.1% by liquid chromatography to give a 69.5% corrected yield.

B. Non-Catalyzed Reaction

The non-catalyzed reaction was run the same as the reaction in part A except no phenol was dissolved in the cumene hydroperoxide. The same temperature program was used for the reaction except the reaction had to be run 5¼ hours at 45° C. instead of 1 1/5 hours to complete the reaction. The volatiles were steam distilled out of the crude product under vacuum (see Example III). The organic residue after isolation and drying weighed 57.0 grams and assayed 84.0% by liquid chromatography to give a 57% corrected yield.

Table I gives a summary of the % dicumyl peroxide in the reaction mixtures after various lengths of reaction. The values in parenthesis are normalized for the amount of phenol added to the system, so a direct comparison can be drawn.

TABLE I

| % Dicumyl Peroxide in Reaction Mixtures | | | |
|---|---|---|---|
| Reaction Time | Temp °C. | Phenol Catalyzed | Non-catalyzed |
| 5 minutes | 15° | 6.4 (6.8) | 1.7 |

TABLE I-continued

% Dicumyl Peroxide in Reaction Mixtures

| Reaction Time | Temp °C. | Phenol Catalyzed | Non-catalyzed |
|---|---|---|---|
| ½ hour | 30° | 25.7 (27.0) | 7.5 |
| 1 hour | 45° | 53.7 (56.5) | 23.5 |
| 1¼ hours | 45° | 60.2 (63.3) | 36.4 |
| 1¾ hours | 45° | 61.4 (64.5)* | |
| 2 hours | | | 43.8 |
| 3 hours | | | 52.6 |
| 4 hours | | | 57.6 |
| 5 hours | | | 59.6 |
| 5½ hours | | | 60.8 |
| 5¾ hours | | | 61.3* |

*Reaction complete

EXAMPLE III

Steam Stripping of Dicumyl Peroxide

This example describes the procedure for steam distilling off the volatiles from the crude washed dicumyl peroxide and the isolation and drying of the final product.

The washed dicumyl peroxide was transferred to a 2 liter 3-neck flask with a thermometer, steam inlet line, magnetic stirrer and distilling head connected to a condenser, receiver and dry ice trap connected to a manometer and vacuum pump. Approximately 400 mls of water were added to the flask, the magnetic stirrer activated and a vacuum of 100–120 mm Hg drawn on the system. Then the steam line was cracked open and the glass inlet lowered below the level of the liquid. The volatile components were steam distilled out of the flask and collected in the receiver and the dry ice trap. The temperature in the flask was held around 55°–60° C. throughout the steam distillation. The steam stripping required approximately 1½ hours at 55°–60° C. and 100–120 mm Hg. At the end of the steam stripping (no organic film in the condenser), the steam inlet was raised above the level of the liquid, the steam shut off and then the vacuum pump was turned off. The vacuum was released and the contents of the flask cooled to about 30° C. The mixture was transferred to a 2 liter separatory funnel and the stripped dicumyl peroxide taken up in 400 mls of pentane by shaking for 5 minutes. The pentane layer was separated, dried over anhydrous sodium sulfate, filtered and the pentane stripped off under reduced pressure on a rotating evaporator. A water aspirator was used to remove most of the pentane and the last traces were removed by stripping with a vacuum pump at 50° C. The residue was weighed and assayed by liquid chromatography using an internal standard.

EXAMPLE IV

Preparation of Dicumyl Peroxide Using Various Amounts of Phenol

This example demonstrates how varying the amount of phenol catalyst in the reaction effects the reaction time required to complete the reaction. All the reactions were monitored by gas chromatography to determine when the reactions were complete.

A series of 5 reactions were run where the amount of phenol added was varied from 2 to 10 grams in 2 gram intervals. The reactions were run at 40° C. and the reaction time varied from greater than 5½ hours to 1½ hours. The reactions were run in the 200 ml jacketed reactor described in Example II. The phenol was dissolved in 47.2 grams (0.4 m) alpha-methylstyrene and added to the reactor. The t-cumyl chloride, 5.0 grams (0.0323 m), was added to the reactor and the temperature adjusted to 25° C. The 81.9% cumene hydroperoxide, 58.6 grams (0.315 m), was added with vigorous stirring over 5 minutes at 25° C. from an addition funnel. At the end of the addition the temperature was raised to 40° C. and the reaction stirred until reaction was complete, i.e. less than 1% unreacted cumene hydroperoxide in the VPC scan. (In the case of the run made with only 2 grams of phenol the reaction was terminated after 5½ hours although there was still about 4% cumene hydroperoxide present in the reaction mixture due to insufficient time to complete the reaction. This accounts for the low yield in this run). The reactions were terminated and worked up in the usual manner. The results are illustrated in Table II.

TABLE II

Effect of the Amount of Phenol Present on the Reaction Time

| Run # | Grams $C_6H_5OH$ added | Reaction Time at 40° C. | Stripped Weight | L. C. Assay | Corrected % Yield |
|---|---|---|---|---|---|
| 1 | 2 | 5½ hours* | 57.1 | 97.3 | 65.3 |
| 2 | 4 | 5 hours | 61.0 | 95.9 | 68.8 |
| 3 | 6 | 2½ hours | 64.3 | 96.3 | 72.8 |
| 4 | 8 | 1¾ hours | 64.8 | 96.0 | 73.2 |
| 5 | 10 | 1½ hours | 66.0 | 95.7 | 74.2 |

*Reaction incomplete

EXAMPLE V

Preparation of Dicumyl Peroxide Using Various Amounts of Phenol and Excess Cumene Hydroperoxide This example also demonstrates how varying the amount of phenol catalyst in the reaction effects the reaction time required to complete the reaction but in this reaction an excess of cumene hydroperoxide is used. All the reactions were monitored by gas chromatography to determine when the reactions were complete.

A series of 4 reactions were run where the amount of phenol added was varied from 0 to 3 grams in 1 gram intervals. The reactions were run for ½ hour at 30°, the temperature raised to 45° C. and the reaction completed at 45° C. The reaction time at 45° C. varied from 3½ hours to 1¼ hours.

The reactions were run in a 250 ml 3-neck round bottom flask equipped with a magnetic stirrer, thermometer, condenser and addition funnel. The phenol was dissolved in 27.2 grams (0.231 m) alpha-methylstyrene in the reaction flask. The t-cumyl chloride, 5.8 grams (0.37 m), was added to the flask and the temperature adjusted to 20° C. Then 81.9% cumene hydroperoxide, 58.6 grams (0.315 m), was added with vigorous stirring over 5 minutes at 20° C. from the addition funnel. At the end of the addition the temperature was raised to 30° C. for ½ hour and then raised to 45° C. and the reaction stirred until reaction was complete, i.e. less than 1% unreacted cumene hydroperoxide in the VPC scan. The reactions were terminated and worked up in the usual manner. The results are illustrated in Table III. The corrected % yields are based on the cumene hydroperoxide despite the fact it was used in excess.

TABLE III

Effect of the Amount of Phenol Present on the Reaction Time

| Run # | Grams C₆H₅OH Added | Reaction Time at 45° C. | Stripped Weight | L. C. Assay | Corrected % Yield |
|---|---|---|---|---|---|
| 1 | 0 | 3½ hours | 51.2 | 91.7 | 55.2 |
| 2 | 1 | 2½ hours | 52.2 | 92.6 | 56.9 |
| 3 | 2 | 1¾ hours | 51.4 | 93.8 | 56.8 |
| 4 | 3 | 1¼ hours | 52.7 | 93.3 | 57.9 |

EXAMPLE VI

Preparation of Dicumyl Peroxide Using Liquified Phenol as a Catalyst

This example demonstrates that liquified phenol, which contains about 9% water to keep it in the liquid state, is also a very effective catalyst for the preparation of dicumyl peroxide.

Into a 2-liter jacketed reactor equipped with a mechanical stirrer, thermometer, water-cooled condenser and addition funnel, were added 141 grams (1.2 m) alpha-methylstyrene, 229.6 grams (1.26 m) of 83.3% cumene hydroperoxide and 26.7 grams (0.255 m) of 91% aqueous phenol (liquified). A solution of 26.8 grams (0.173 m) t-cumyl chloride in 47 grams (0.4 m) alpha-methylstyrene was transferred to the addition funnel. The t-cumyl chloride solution was added to the stirred hydroperoxide solution over 5 minutes while adjusting the reaction temperature at 19°–20° C. by circulating water through the reactor jacket. The reaction temperature was raised from 20° to 25° C. over 20 minutes, the reaction stirred 20 minutes at 25° C., the reaction temperature raised to 35° C. over 20 minutes, the reaction stirred 15 minutes at 35° C., the reaction temperature raised to 45° C. over 15 minutes and the reaction stirred 45 minutes at 45° C. to complete the reaction. The reaction was terminated by adding 35 mls of water, stirring 5 minutes, adding 150 mls of Na₂SO₃ solution and stirring another 5 minutes. The aqueous layer was separated and the organic layer was washed successively with 220 ml portions of 30% NaOH (twice), and water (4 times). After drying, the crude product weighed 395 grams and assayed 65.7% by liquid chromatography to give a 76.5% yield.

EXAMPLE VII

Preparation of Cumyl t-Butyl Peroxide

This example demonstrates the difference between a phenol catalyzed reaction and a non-catalyzed reaction in the preparation of cumyl t-butyl peroxide. The reactions were monitored by gas chromatography to determine the extent of reaction.

A. Phenol Catalyzed Reaction

Into a 500 ml erlenmeyer flask equipped with a magnetic stirrer and a thermometer were added 141.6 grams (1.2 m) alpha-methylstyrene, 92.7 grams (0.945 m) 91.9% t-butylhydroperoxide and 18.0 grams (0.192 m) of phenol. The solution was stirred 10 minutes and the temperature adjusted to 18° C. To this solution was added 13.4 grams (0.086 m) of t-cumyl chloride over 8 minutes with the temperature slowly rising to 22° C. The flask was placed in a cool water bath and the reaction stirred for ½ hour at 25° C. The water bath was removed and the temperature rose to 35° C. over the next ½ hour and to 38° C. over the next 15 minutes where it leveled off and remained constant for the next hour and then slowly dropped to 35° C. over the next 1½ hours. After a total of 3¾ hours stirring the reaction was essentially complete so 150 mls of water were added, the mixture stirred 15 minutes to hydrolyze the t-cumyl chloride and then 30 mls of 50% NaOH were added. The brown mixture was stirred 15 minutes and the brown aqueous layer separated. The organic layer was washed with 100 mls of 15% NaOH then 3 times with 100 mls of water and once with 100 mls of saturated NaHCO₃ solution. The crude product was dried over anhydrous sodium sulfate and filtered. The drying agent was rinsed down with pentane and the pentane stripped off on a rotating evaporator. The residue weighed 224.0 grams and assayed 77.5% cumyl t-butyl peroxide by gas chromatography for an 88.5% yield. The pure product was isolated by fractional distillation under vacuum. A summary of the extent of reaction at various time intervals from integration of the VPC scans can be found in Table IV. The values in parenthesis are values corrected for the amount of phenol in the system so they can be directly compared to the non-catalyzed system.

B. Non-Catalyzed Reaction

Into a 500 ml erlenmeyer flask equipped with a magnetic stirrer and a thermometer were added 141.6 grams (1.2 m) alpha-methylstyrene and 92.7 grams (0.945 m) 91.9% t-butylhydroperoxide. The solution was stirred 10 minutes and the temperature stabilized at 24° C.

To this solution was added 13.4 grams (0.086 m) of t-cumyl chloride over 7 minutes. The reaction was stirred 30 minutes at 25° C. and then the flask was placed in a warm water bath and the temperature raised to 35° C. over ½ hour. The reaction was then stirred 3 hours at approximately 35° C. Since there was a large amount of unreacted t-butylhydroperoxide left, the reaction was stirred 2 hours at 40°–45° C., allowed to stand overnight at room temperature and then stirred another hour at 40°–45° C. Since there was still about 25% of the t-butylhydroperoxide unreacted an additional 3 grams of t-cumyl chloride were added and the reaction stirred 3 hours at 40° C.±5° C. Another 3 grams of t-cumyl chloride were added and the reaction was stirred another hour at 40° C.±5°. Since very little reaction was occurring the reaction was terminated by adding 100 mls of water followed by 30 mls of 50% NaOH 5 minutes later. The same workup procedure was used as in part A. The crude product weighed 211 grams and assayed 67.9% for a 72% yield. Thus using the non-catalyzed system, the reaction time was much longer, higher temperatures had to be employed, the reaction did not go to completion, the yield was lower and the assay was lower. A summary of the extent of reaction at various time intervals can be found in Table IV.

TABLE IV

Preparation of Cumyl t-Butyl Peroxide

| Reaction Time After Addition | Temp °C. | Phenol Catalyzed | | | | Non-Catalyzed | | |
|---|---|---|---|---|---|---|---|---|
| | | % α-MeSty | % Phenol | % t-BuOOH | % Product | % α-MeSty | % t-BuOOH | % Product |
| 10 mins | 25 | 32.5 (36.1) | 10.2 | 23.7 (26.4) | 17.8 (19.7) | 49.2 | 30.9 | 10.8 |
| 30 mins | 25 | 27.4 (30.5) | 10.1 | 21.5 (23.9) | 25.7 (28.6) | 45.5 | 31.2 | 13.5 |
| 1 hour | 35 | 19.7 (21.9) | 10.4 | 9.7 (10.8) | 44.3 (49.3) | 38.6 | 28.3 | 19.2 |
| 2 hours | 35 | 15.8 (17.6) | 10.2 | 4.7 (5.2) | 49.3 (54.6) | 32.2 | 24.2 | 31.0 |
| 3 hours | 35 | 13.6 (15.0) | 10.1 | 2.9 (3.2) | 53.5 (59.5) | 30.6 | 22.5 | 36.1 |
| 3¾ hours | 35 | 13.0 (14.4) | 9.9 | 2.6 (2.9) | 55.5 (61.7) | | | |
| 4 hours | 40 | | | | | 33.3 | 20.9 | 40.8 |
| 6 hours | 40 | | | | | 28.85 | 16.5 | 50.0 |
| 1 hour* | 40 | | | | | 20.3 | 7.5 | 54.6 |

*1 hour after 3rd addition of t-cumyl chloride. Reaction terminated at this point.

EXAMPLE VIII

Preparation of Cumyl t-Amyl Peroxide

This example demonstrates the difference between a phenol catalyzed reaction (at two levels of phenol) and a non-catalyzed reaction in the preparation of cumyl t-amyl peroxide. The reactions were monitored by gas chromatography to determine the extent of reaction.

A. Phenol Catalyzed Reaction-High Level of Phenol

Into the 200 ml jacketed reactor described in Example II were added 15.0 grams (0.127 m) alpha-methylstyrene, 15.5 grams (0.1 m) 67.3% t-amyl hydroperoxide and 3.8 grams (0.041 m) phenol. The mixture was stirred to obtain a clear solution and the temperature was adjusted to 20° C. by pumping cool water through the reactor jacket. To this solution was added 1.4 grams (0.009 m) of t-cumyl chloride from the addition funnel over 10 minutes while holding the temperature at 21°-22° C. The reaction was stirred 5 minutes at 22° C., the temperature raised to 25° C. and the reaction stirred ½ hour at 30° C., ½ hour at 35° C., 1½ hours at 40° C. and ½ hour at 45° C. for a total reaction time of 3½ hours. At this point essentially all the t-amyl hydroperoxide had been consumed. The reaction was terminated by adding 25 mls of water, stirring 5 minutes, adding 5 mls of 50% NaOH, stirring another 5 minutes and then separating the aqueous caustic layer. The organic layer was washed with saturated NaHCO$_3$ solution, water, 15% NaHSO$_3$, saturated NaHCO$_3$ again and water. The dried material weighed 24.6 grams and contained 54.6% cumyl t-amyl peroxide for a corrected yield of 13.4 grams and a 60.5% yield. The pure cumyl t-amyl peroxide was isolated by fractional distillation under vacuum.

B. Phenol Catalyzed Reaction—Low Level of Phenol

This reaction was run the same as the reaction in part A except the mole ratio of phenol to hydroperoxide was cut in half. The same temperature programs was used for the reaction except the reaction had to be run 3 hours at 45° C. instead of ½ hour at 45° C. to essentially complete the reaction. The % yield was only 49.9%.

C. Non-Catalyzed Reaction

The reaction was run the same as the reaction in part A except no phenol was used. The same temperature program was used for the reaction except the reaction was run 3½ hours at 45° C. instead of ½ hour and only about ½ of the t-amyl hydroperoxide had reacted. The reaction was terminated at this point due to a lack of time. The % yield was only 20.6%.

Table V gives a summary of the % of cumyl t-amyl peroxide in the reaction mixture at various stages of the reaction. The values in parenthesis are normalized for the amount of phenol added to the system so that a, direct comparison can be drawn.

TABLE V

| | | % Cumyl t-Amyl Peroxide in Reaction Mixture | | |
|---|---|---|---|---|
| Reaction Time | Temp. °C. | Phenol Catalyzed | | Non-Catalyzed |
| | | High Level | Low Level | |
| ½ hour | 25° | 18 (20.5) | 7.4 (7.9) | 2.4 |
| 1 hour | 30° | 29.7 (34.2) | 14.8 (15.8) | 5.4 |
| 1½ hours | 35° | | 22.1 (23.7) | 9.4 |
| 2 hours | 40° | 46.2 (53.3) | 29.2 (31.3) | 13.6 |
| 2½ hours | 40° | 50.0 (58.0) | 33.9 (36.4) | |
| 3 hours | 40° | 50.8 (59.1) | 37.7 (40.5) | 16.4 |
| 3½ hours | 45° | 53.4 (61.9)* | 40.3 (43.1) | |
| 4 hours | 45° | | 42.8 (45.7) | 21.9 |
| 6 hours | 45° | | 53.2 (55.9)* | 25.6 |
| 6½ hours | 45° | | | 26.1 |

*Reaction complete

EXAMPLE IX

Preparation of Cumyl t-Hexyl Peroxide

This example demonstrates the difference between a phenol catalyzed reaction (at two levels of phenol) and a non-catalyzed reaction in the preparation of cumyl t-hexyl peroxide. The reactions were monitored by gas chromatography to determine the extent of reaction.

A. Phenol Catalyzed Reaction—High Level of Phenol

Into the 200 ml jacketed reactor described in Example II were added 15.6 grams (0.13 m) alpha-methylstyrene, 15.0 grams (0.104 m) 82% t-hexyl hydroperoxide and 4.0 grams (0.043 m) phenol. The mixture was stirred to obtain a clear solution and the temperature was adjusted to 20° C. To this solution was added 1.5 grams (0.0095 m) of t-cumyl chloride from the addition funnel over 5 minutes while holding the temperature at 21°-22° C. The reaction self-exothermed to 25° C. over 10 minutes and then was stirred an additional ½ hour at 25° C. The reaction was then stirred 80 minutes at 35° C. and 90 minutes at 40° C. at which point the reaction was complete. The reaction was terminated by adding 25 mls of water, stirring 5 minutes, adding 5 mls of 50% NaOH, stirring another 5 minutes and separating the aqueous caustic layer. The organic layer was successively washed with 25 mls of 15% NaOH, saturated NaHCO$_3$ solution, water, 15% NaHSO$_3$ solution, saturated NaHCO$_3$ solution and water. After drying with anhydrous sodium sulfate the crude product weighed 26.7 grams and contained 80.6% cumyl t-hexyl peroxide for a corrected yield of 21.5 grams and a 87.8% yield. The pure cumyl t-hexyl peroxide was isolated by fractional distillation under vacuum.

B. Phenol Catalyzed Reaction—Low Level of Phenol

This reaction was run the same as the reaction in part A except only 2.0 grams (0.021 m) of phenol were used. The same temperature program was used for the reaction except the reaction had to be stirred an additional 95 minutes at 45° C. to complete the reaction. The crude product weighed 26.4 grams and assayed 74.0% cumyl t-hexyl peroxide for a corrected yield of 19.5 grams and a % yield of 79.7%.

C. Non-Catalyzed Reaction

The reaction was run the same as the reaction in part A except no phenol was used. The cumyl chloride was added over 5 minutes at 20°-21° C. After 40 minutes stirring the temperature had only risen to 23° C. The reaction was warmed to 35° C., stirred 80 minutes at 35° C., 90 minutes at 40° C. and 3¼ hours at 45° C. At this point about 25% of the t-hexyl hydroperoxide had still not reacted but the reaction was terminated and worked up as in Part A due to lack of time. The crude product weighed 19.8 grams and assayed 29.8% for a corrected yield of 5.9 grams and a % yield of 24%.

Table VI gives a summary of the % cumyl t-hexyl peroxide in the reaction at various stages of the reaction. The values in parenthesis are normalized for the amounts of phenol added to the system so that a direct comparison can be made.

TABLE VI

| | | % Cumyl t-Hexyl Peroxide in Reaction Mixture | | |
|---|---|---|---|---|
| Reaction Time | Temp. °C. | Phenol Catalyzed High Level | Low Level | Non-Catalyzed |
| 1 hour | 35° | 49.0 (53.6) | 20.7 (21.6) | 3.1 |
| 1½ hours | 35° | 62.0 (68.3) | 31.4 (32.8) | |
| 2 hours | 35° | 71.4 (77.8) | 41.0 (42.4) | 8.8 |
| 3 hours | 40° | 75.5 (83.7) | 55.1 (57.8) | 13.3 |
| 3½ hours | 40° | 77.2 (84.6)* | 60.2 (63.1) | 15.3 |
| 4 hours | 45° | | 64.9 (67.5) | |
| 4½ hours | 45° | | 65.8 (69.0) | 19.4 |
| 5½ hours | 45° | | 70.8 (74.2) | 21.6 |
| 6½ hours | 45° | | 74.9 (78.5)* | 24.7 |

*Reaction complete

EXAMPLE X

Preparation of Cumyl t-Octyl Peroxide

Into the 200 ml jacketed reactor described in Example II were added 18.0 grams (0.152 m) alpha-methylstyrene, 18.4 grams (0.11 m) 87.6% 1,1,3,3-tetramethylbutyl hydroperoxide and 4.6 grams (0.048 m) phenol. The mixture was stirred to obtain a clear solution and the temperature was adjusted to 20° C. To this solution was added 1.7 grams (0.011 m) of t-cumyl chloride from the addition funnel over 5 minutes while holding the temperature at 20°-21° C. The reaction was stirred 5 minutes at 21°-22° C., warmed to 25° C. and stirred ½ hour at 25° C., ½ hour at 30° C., ½ hour at 35° C., 1½ hours at 40° C. and finally ½ hour at 45° C. At this point the t-octyl hydroperoxide had been completely consumed and the reaction was terminated by adding 50 mls of water, stirring 5 minutes, adding 10 mls of 50% NaOH, stirring another 5 minutes and separating the aqueous caustic layer. The organic layer was successively washed with 50 mls 15% NaOH, saturated NaHCO₃ solution, H₂O, 15% NaHSO₃ solution, saturated NaHCO₃ solution and water. After drying over anhydrous sodium sulfate the crude product weighed 32.6 grams and contained 72.6% cumyl t-octyl peroxide for a corrected yield of 23.7 grams and a 81.5% yield.

The crude product was purified by steam distilling off the volatiles under vacuum and chromatographing the residue over alumina using pentane as the eluent.

EXAMPLE XI

Preparation of 2-t-Cumylperoxy-2-methyl-4-hydroxypentane

The reaction was run in the same manner as the preparation of cumyl t-octyl peroxide except 16.1 grams (0.12 m) of 2-hydroperoxy-2-methyl-4-hydroxypentane were used instead of the t-octyl hydroperoxide. The reaction was stirred ½ hour at 25° C., ½ hour at 30° C., ½ hour at 35° C., 1½ hours at 40° C. and finally 3 hours at 45° C. to complete the reaction. The reaction was worked up in the normal manner. The crude product weighed 28.8 grams and assayed approximately 67% for a 64% yield.

EXAMPLE XII

Preparation of 3-(t-Cumylperoxy)-3-methylbutyne-1

The reaction was run in the same manner as the preparation of cumyl t-octyl peroxide except 16.4 grams (0.12 m) of 73.3% 3-hydroperoxy-3-methylbutyne-1 were used instead of the t-octyl hydroperoxide. The reaction was stirred ½ hour at 25° C., ½ hour at 30° C., ½ hour at 35° C., 1½ hours at 40° C. and finally ½ hour at 45° C. to complete the reaction. The reaction was worked up in the normal manner. The crude product weighed 29.8 grams and assayed approximately 74% for an 84% yield.

EXAMPLE XIII

Preparation of 2,5-Di-t-cumylperoxy-2,5-dimethylhexane

Into a 100 ml 3-neck round bottom flask were added 35.4 grams (0.3 m) alpha-methylstyrene and 3.8 grams (0.04 m) phenol. The flask was equipped with a magnetic stirrer, thermometer, condenser and addition funnel. The phenol was dissolved in the alpha-methylstyrene with stirring at 20° C. To this solution was added 9.1 grams (0.05 m) of 98% 2,5-dihydroperoxy-2,5-dimethylhexane. To the resulting slurry was added 3.1 grams (0.02 m) t-cumyl chloride dropwise from the addition funnel. The temperature slowly rose to 29° C. over ½ hour and a clear solution formed. At this point an additional 4.5 grams (0.025 m) of the dihydroperoxide was added. The temperature slowly dropped to 26° C. over the next 1¼ hours at which point the solution became clear again. Another 4.5 grams (0.025 m) of the dihydroperoxide was added. The reaction was stirred 2¼ hours at 26° C. but the solution was still cloudy so it was warmed to 35° C. (solution cleared) and stirred at 30°-35° C. for another hour. The reaction was terminated by adding 40 mls of water and stirring 10 minutes. The contents of the flask were poured into a 125 ml erlenmeyer flask, the reaction flask rinsed out with a small amount of pentane and 10 mls of water. With rapid stirring, 10 mls of 50% NaOH were added and the mixture stirred 15 minutes and the aqueous layer separated. The organic layer was washed successively with 50 ml portions of water, saturated NaHCO₃ solution and water. The volatiles were steam distilled out of the crude product under vacuum. The organic residue after isolation and drying weighed 36.5 grams for an 88% crude yield. The product slowly solidified into a white solid. The crude product was further purified by recrystallization from methanol to give a white powder. The compound was not shock sensitive and had a melting point of 38°–39° C.

EXAMPLE XIV

Preparation of
2,5-Di-t-cumylperoxy-2,5-dimethylhexyne-3

Into a 250 ml 3-neck round bottom flask, equipped with a condenser, thermometer, magnetic stirrer and addition funnel, were added 35.4 grams (0.3 m) alpha-methylstyrene and 6.0 grams (0.063 m) phenol. The phenol was dissolved in the alphamethylstyrene with stirring at 25° C. To this solution was added 12.7 grams (0.05 m) of 68% wet 2,5-dihydroperoxy-2,5-dimethyl-hexyne-3 and the mixture stirred for 10 minutes before adding 6.2 grams (0.04 m) t-cumyl chloride from the dropping funnel over 2 minutes. The reaction mixture was stirred ½ hour at 24°–25° C. and a clear solution resulted. An additional 3.2 grams (0.0125 m) of the dihydroperoxide were added. The temperature slowly rose from 24° C. to 31° C. over 15 minutes. The reaction was stirred an additional hour and the temperature gradually dropped back to 24° C. and a clear solution formed. Another 3.2 grams (0.0125 m) of the dihydroperoxide were added. The reaction was stirred an additional 2½ hours at 24°–25° C. The solution was still cloudy so 1 gram of t-cumyl chloride was added, the reaction warmed to 35° C. and stirred 2 hours at 30°–35° C. The reaction was terminated by adding 50 mls water, stirring 10 minutes, adding 10 mls NaOH, stirring 15 minutes and separating the aqueous phase. The organic layer was washed successively with 50 ml portions of water, saturated NaHCO$_3$ solution and water. The volatiles were steam distilled out of the crude product under vacuum. The organic residue after isolation and drying weighed 41.7 grams. It was recrystallized from methanol at −20° C. to give 31.0 grams of a white powder. The compound was not shock sensitive and had a melting point of 49°–51° C.

EXAMPLE XV

Preparation of Dicumyl Peroxide Using Methanol as a Catalyst

In this example we attempted to use methanol as a catalyst for the preparation of dicumyl peroxide. The reaction was monitored by gas chromatography to determine the extent of reaction. Into the 200 ml jacketed reactor described in Example II were added 27.2 grams (0.23 m) alpha-methylstyrene and 5.8 grams (0.0375 m) t-cumyl chloride. The stirrer was activated and with the temperature around 25° C., 56.5 grams (0.315 m) of 85% cumene hydroperoxide and 5 mls of methanol were quickly added. The reaction temperature was brought up to 45° C. over 3 minutes by circulating warm water through the reactor jacket. The reaction was stirred 1½ hours at 45° C. at which point the hydroperoxide was completely consumed. The reaction mixture was cooled to 30° C. and washed with 50 mls of 20% sodium sulfite solution for 10 minutes, separated, washed twice with 50 ml portions of 30% NaOH, once with saturated NaHCO$_3$ and three times with water. The volatiles were steam distilled out of the crude product under vacuum. The crude residue after isolation and drying weighed 35.7 grams and assayed 91.1% by liquid chromatography to give a 38.2% corrected yield. The crude product contained 8.7% cumyl methyl ether.

The reaction ran faster than normal but there was a greater degree of decomposition of the cumene hydroperoxide, the yield was lower and there was a considerable amount of cumyl methyl ether formed from the reaction of the methanol with the t-cumyl chloride.

EXAMPLE XVI

Preparation of Dicumyl Peroxide Using t-Butanol as a Catalyst

In this example we tried to use t-butanol as a catalyst for the preparation of dicumyl peroxide. The reaction was monitored by gas chromatography to determine the extent of reaction.

The reaction was run the same as Example XV except 5 mls of t-butanol were used instead of 5 mls of methanol. The reaction had to be stirred 3½ hours at 45° C. to complete the reaction. This is 2 hours longer than required in the methanol reaction and about ½ to ¾ hours longer than when no additive is used. The reaction was worked up the same as in Example XV. The volatiles were steam distilled out of the crude product under vacuum. The crude residue after isolation and drying weighed 45.7 grams and assayed 88.9% by liquid chromatography to give a 48.5% corrected yield.

The t-butanol did not catalyze the reaction in fact it slowed it down somewhat and the yield was slightly low.

EXAMPLE XVII

Preparation of Dicumyl Peroxide Using Ethanol as a Catalyst

In this example we attempted to use ethanol as a catalyst for the preparation of dicumyl peroxide. The reaction was monitored by gas chromatography to determine the extent of reaction. Into the 200 ml jacketed reactor described in Example II were added 27.2 grams (0.23 m) alpha-methylstyrene and 5.8 grams (0.0375 m) t-cumyl chloride. The stirrer was activated and with the temperature around 25° C., 56.5 grams (0.315 m) of 85% cumene hydroperoxide and 5 mls of ethanol were quickly added. The reaction temperature was brought up to 40° C. over 3 minutes by circulating warm water through the reactor jacket. The reaction was stirred 2½ hours at 40° C. at which point the hydroperoxide was essentially consumed. The reaction mixture was cooled to 30° C. and 50 mls of a solution composed of 3 parts methanol and 1 part 50% NaOH by volume was added and the mixture stirred for 20 minutes, 50 mls of water and 50 mls of hexane added, the mixture stirred 1 minute and the aqueous caustic layer separated. The hexane solution was washed successively with 50 ml portions of water, 5% NaHSO$_3$, saturated NaHCO$_3$ and water. The volatiles were steam distilled out of the crude product under vacuum, the crude residue after isolation and drying weighed 42.1 grams and assayed 91.8% by liquid chromatography to give a 45.5% corrected yield.

The addition of the ethanol reduced the reaction time slightly but it gave approximately 25% lower yield.

EXAMPLE XVIII

Preparation of Dicumyl Peroxide Using Acetic Acid as a Catalyst

In this example we attempted to use acetic acid as a catalyst for the preparation of dicumyl peroxide. The reaction was monitored by gas chromatography.

Into the 200 ml jacketed reactor described in Example II were added 47.2 grams (0.4 m) alpha-methylstyrene and 6.7 grams (0.0433 m) t-cumyl chloride. The stirrer was activated and the temperature adjusted to 15° C. by circulating cold water through the reactor jacket. To the cooled solution was added 57.4 grams (0.315 m) of 83.5% cumene hydroperoxide. The mixture was stirred 5 minutes and then 6.0 grams (0.1 m) of acetic acid were added dropwise from the addition funnel over 5 minutes at 15°-17° C. The reaction was stirred ½ hour at 15°-20° C., the temperature raised to 30° C. and the reaction stirred 1 hour at 30° C. and the temperature raised to 45° C. The reaction had to be stirred 5 hours at 45° C. to complete the reaction. The reaction was terminated by adding 75 mls of water, stirring 15 minutes, adding 15 mls of 50% NaOH and stirring another 15 minutes. The aqueous layer was separated and the organic layer was washed with water until neutral. The volatiles were steam distilled out of the crude product under vacuum. The crude residue after isolation and drying weighed 56 grams and assayed 91.5% by liquid chromatography to give a 60% yield.

The reaction took much longer than the normal reaction and the yield was about 10-15% lower than the phenol catalyzed reactions run under similar conditions.

EXAMPLE XIX

Preparation of Dicumyl Peroxide Using Acetone as a Catalyst

In this example we attempted to use acetone as a catalyst for the preparation of dicumyl peroxide. The reaction was monitored by gas chromatography.

Into the 200 ml jacketed reactor described in Example II were added 27.2 grams (0.23 m) alpha-methylstyrene and 5.8 grams (0.0433 m) t-cumyl chloride. The stirrer was activated and the temperature adjusted to 20° C. To this solution was added 56.0 grams (0.315 m) of 85% cumene hydroperoxide and then 5 mls of acetone were added dropwise from the addition funnel. The reaction temperature rose to 22° C. upon addition of the acetone. The reaction mixture was warmed to 40° C. over 10 minutes, stirred 85 minutes at 40° C. and 90 minutes at 45° C. at which point most of the cumene hydroperoxide had been consumed. The reaction was terminated by adding 25 mls of water and then slowly adding 50 mls of 15% NaHSO$_3$. The aqueous layer was separated and the organic layer was washed successively with 50 ml portions of 30% NaOH, water, saturated NaHCO$_3$ solution and water. The volatiles were steam distilled out of the crude product under vacuum. The organic residue after isolation and drying weighed 25.0 grams and assayed 84.5% by liquid chromatography to give a 34.2% corrected yield.

The reaction was not catalyzed by the acetone, the yield of dicumyl peroxide was low, the assay of the steam stripped dicumyl peroxide was low and a considerable amount of di-t-cumyl-peroxypropane was formed.

EXAMPLE XX

Preparation of Di-cumyl Peroxide from t-Cumyl Chloride and Cumene Hydroperoxide Using T-Butanol as an Acid Binding Agent This example demonstrates that t-butanol is not as efficient an acid binding agent as alpha-methylstyrene and that the Kato process does not work very well for acid sensitive hydroperoxides. The reaction was monitored by gas chromatography.

Into a 100 ml 3-neck round bottom flask, equipped with a magnetic stirrer, thermometer, water-cooled condenser and dropping funnel, were added 29.4 grams (0.16 m) of 83% cumene hydroperoxide and 25 grams (0.34 m) t-butanol. The temperature of the solution was adjusted to 20° C. and 26.0 grams (0.165 m) t-cumyl chloride were transferred to the dropping funnel. A dropwise addition of the cumyl chloride was begun. After 3 minutes there was no noticeable exotherm so the addition was stopped and the temperature of the solution raised to 30° C. with a warm water bath. The addition was restarted and the remainder of the t-cumyl chloride was added over 18 minutes with the temperature holding at 30° C. VPC analysis indicated the presence of 28% dicumyl peroxide in the reaction mixture. The temperature remained constant for most of the next hour and then rose to 41° C. toward the end of the hour. It was cooled to 35° C. to stop the exotherm and then warmed back up to 40° C. VPC analysis indicated the cumene hydroperoxide was completely consumed at this point. The reaction was stirred an additional hour at 45° C.±and then stirred into 100 ml warm H$_2$O. The aqueous layer was separated washed with another 100 ml warm H$_2$O twice. In the second washing 25 ml of 50% NaOH were added and the mixture stirred 10 minutes at 50° C. The aqueous layer was separated and the organic layer was washed successively with water (3 times), saturated NaHCO$_3$ solution and water. The volatiles were steam distilled out of the crude product under vacuum. The organic residue after isolation and drying weighed 15.5 grams and assayed 83.6% by liquid chromatography to give a 30.0% corrected yield.

A VPC scan at the end of the reaction period indicated there was approximately 21% alpha-methylstyrene, 13% phenol and 32% dicumyl peroxide present. This indicates that a considerable amount of the cumyl chloride eliminated HCl to form alpha-methylstyrene and a considerable amount of the cumene hydroperoxide decomposed in the presence of the HCl to form phenol.

EXAMPLE XXI

Preparation of Dicumyl Peroxide Using p-Cresol as a Catalyst

This example demonstrates that substituted phenols also work as catalysts in the preparation of dicumyl peroxide.

A solution of 6.9 grams (0.064 m) p-cresol in 47.2 grams (0.4 m) alpha-methylstyrene was prepared and filtered to remove any iron particles. The solution was transferred to a 200 ml 3-neck round bottom flask equipped with a thermometer, magnetic stirrer, dropping funnel containing 58.6 grams (0.315 m) of 81.9% cumene hydroperoxide and a water-cooled condenser. To the alpha-methylstyrene was added 6.7 grams (0.0433 m) t-cumyl chloride and the temperature of the resulting solution was adjusted to 25° C. The cumene hydroperoxide was added from a dropping funnel over 5 minutes at 25° C. Without a bath around the flask, there was no apparent exotherm during the addition but the temperature began to slowly rise after the addition was complete. After 25 minutes the temperature had risen to 37° C. and after 40 minutes it had reached 45° C. At this point the reaction was cooled to 40° C. and the bath removed. The temperature dropped to 37° C. over 20 minutes. The reaction was then warmed back up to 47°–48° C. for another 45 minutes to complete the reaction. The reaction was terminated by adding 50 mls of water, stirred 5 minutes, 10 mls of 50% NaOH added, stirred 15 minutes and the aqueous layer separated. The organic layer was washed with water, 15% NaHSO$_3$ solution, water, saturated NaHCO$_3$ solution and water. The volatiles were steam distilled out of the crude product under vacuum. The organic residue after isolation and drying weighed 62.2 grams and assayed 95.4% by liquid chromatography to give a 69.7% corrected yield.

EXAMPLE XXII

Preparation of Dicumyl Peroxide Using Various Phenols as Catalysts

This example demonstrates that phenols (including napthols) containing inert substituents also work as catalysts and some work better than others depending upon the nature and position of the substituent. The reactions were monitored by gas chromatography to determine when the reaction was complete.

The following general procedure was used for the preparation of the dicumyl peroxide, substituting an equimolar amount of the desired phenol in each case. A control experiment was run without any phenol for comparison sake. All the runs made with Eastman alpha-methylstyrene which seemed to react faster than the commercial grade alpha-methylstyrene we had been using for the other examples. The results are summarized in Table VII.

A solution of phenol or substituted phenol in cumene hydroperoxide was prepared by adding 0.064 mole of the phenol to 57.6 grams (0.315 m) of 83.5% cumene hydroperoxide and stirring until the phenol dissolved.*

*p-Phenylphenol was insoluble in the cumene hydroperoxide and was added directly to the 200 ml reactor just prior to the cumene hydroperoxide addition.

Into a 200 ml jacketed reactor equipped with a mechanical stirrer, thermometer, water-cooled condenser and addition funnel were added 47.2 grams (0.4 m) alpha-methylstyrene and 6.7 grams (0.043 m) t-cumyl chloride. The stirrer was activated and the temperature of the solution was adjusted to 15° C. by circulating cold water through the reactor jacket. After the phenol had dissolved, the cumene hydroperoxide solution was transferred to the addition funnel and added at a uniform rate to the stirred alpha-methylstyrene solution over 10 minutes at 13°–15° C. The reaction mixture was stirred an additional 5 minutes at 15° C., the reaction warmed to 30° C. over 5 minutes and stirred an additional 25 minutes at 30° C. The reaction mixture was then warmed to 45° C. and stirred until the cumene hydroperoxides was consumed (1% or less by VPC). A comparison of the reaction times required at 45° C. to complete the reaction is found in Table VII. Upon consumption of all the hydroperoxide, the reaction was terminated by adding 50 mls of water, stirring 15 minutes, adding 10 mls of 50% NaOH and stirring an additional 10 minutes at 45°–55° C. The aqueous caustic layer was separated and saved for waste disposal. The organic layer was scanned by gas chromatography to see if the aqueous caustic had removed the substituted phenol. If the phenol had not been removed, the organic layer was washed twice for 10 minute periods with 30 mls of methanolic caustic (3 parts by volume methanol and 1 part 50% NaOH). After the phenols had been removed, the organic layer was washed with 50 mls of saturated NaHCO$_3$ and then 3 times with 50 ml portions of water. The organic layer was cooled to room temperature, taken up in 25 mls of pentane, dried over anhydrous sodium sulfate, filtered and the pentane stripped off on a rotating evaporator under reduced pressure. The crude product was weighed, assayed by liquid chromatography and the % yield determined. The volatiles were steam distilled out of the crude product under vacuum. The organic residue after isolation and drying was reassayed.

TABLE VII

Preparation of Dicumyl Peroxide Using Various Phenols as Catalysts

| Exp't # | Phenol Catalyst | R$_x$ Time at 45° C. | Methanolic Caustic Wash Required | Wt. Unstripped Crude Product | L.C. Assay | Corr. % Yield | L.C. Assay Stripped Product |
|---|---|---|---|---|---|---|---|
| 1 | o-Cresol | 1 hr | No | 93.0 | 54.2 | 59.2 | 88.4 |
| 2 | 2,6-Diisopropyl-phenol | 5¼ hrs | Yes | 81.9 | 63.9 | 61.4 | 92.7 |
| 3 | 4-t-Butylphenol | 1¼ hr | No | 85.2 | 63.4 | 63.4 | 92.8 |
| 4 | 4-Chlorophenol | ½ hr | No | 93.9 | 61.4 | 67.7 | 91.1 |
| 5 | 4-Bromophenol | ½ hr | No | 92.8 | 61.8 | 67.3 | 91.2 |
| 6 | 4-Methoxyphenol | 1 hr | No | 99.3 | 59.9 | 69.8 | 89.4 |
| 7 | Phenol | 3¾ hr | No | 94.3 | 59.1 | 65.4 | 89.0 |
| 8 | β-Naphthol | ½ hr | No | 94.9 | 63.7 | 71.0 | 89.4 |
| 9 | 4-Phenylphenol | 1 hr | No | 89.3 | 62.2 | 65.2 | 92.6 |
| 10 | 2-t-Butylphenol | 1¾ hr | Yes | 83.0 | 63.7 | 62.1 | 91.8 |
| 11 | 3-Methoxyphenol | 1¼ hr | No | 100.1 | 64.2 | 75.4 | 89.4 |
| 12 | None | 4 hr | No | 94.9 | 53.1 | 59.1 | 89.0 |

What is claimed is:

1. A process for preparing cumyl peroxides comprising reacting in a temperature range of 10°–50° C. an aliphatic or cycloaliphatic hydroperoxide or aliphatic dihydroperoxide selected from the group consisting of t-butyl hydroperoxide, t-amyl hydroperoxide, t-hexyl hydroperoxide, 1,1,3,3-tetramethylbutyl hydroperoxide, cumene hydroperoxide, cymene hydroperoxide, p-menthane hydroperoxide, 1-methylcyclohexyl hydroperoxide, 1-methylcyclopentyl hydroperoxide, 3-hydroperoxy-3-methylbutyne-1, 2-hydroperoxy-2-methyl-4-hydroxypentane, 1-hydroperoxycyclohexylacetylene, 2,5-dimethyl-2,5-dihydroperoxyhexane, 2,7-dimethyl-2, 7-dihydroperoxyoctane, 2,5-dimethyl-2,5-dihydroperoxyhexyne-3 and diisopropylbenzene dihydroperoxide with an olefin selected from alpha-methylstyrene or a substituted alpha-methylstyrene wherein the substituent is selected from the group consisting of hydrogen, methyl, ethyl, propyl, isopropyl, butyl, t-butyl, amyl, t-amyl, hexyl, chloro, bromo, fluoro, methoxy, ethoxy, propoxy, isopropoxy, phenoxy, phenyl and naphthyl, and a t-cumyl halide corresponding to the hydrohalogenated olefin in the presence of a catalyst selected from the group consisting of phenol, ortho, meta, and paracresols, chlorophenols, bromophenols, methoxyphenols, ethylphenols, isopropylphenols, para-t-butylphenol, paraphenylphenol, 3,4-dichlorophenol, 3,4-dimethylphenol, alpha-naphthol and beta-naphthol under substantially anhydrous conditions.

2. A process for preparing a cumyl peroxide consisting essentially of reacting a hydroperoxide or dihydroperoxide with an olefin and a t-cumyl halide corresponding to the hydrohalogenated olefin in the presence of a phenol or naphthol catalyst under substantially anhydrous conditions in a temperature range of about 10°–50° C., where (a) said hydroperoxide having the formula R—[OOH]$_y$ (III) where y is 1 or 2; when y is 1, R is selected from t-alkyl of 4 to 8 carbons, t-alkynyl of 5 to 8 carbons, t-aralkyl of 9 to 12 carbons or t-cycloalkyl of 6 to 10 carbons; and when y is 2, R is selected from

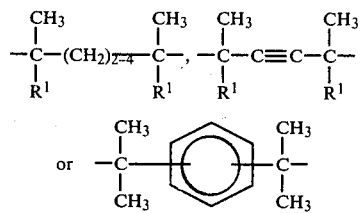

where R$^1$ is selected from alkyl of 1 to 6 carbons;
(b) said olefin having the formula (I)

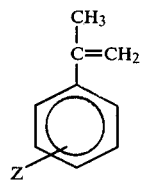

where Z is selected from —H, alkyl of 1 to 6 carbons, Cl-, Br-, F-, alkoxy of 1 to 5 carbons, phenoxy, phenyl or naphthyl;
(c) said t-cumyl halide has the formula (II)

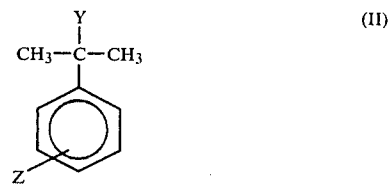

where Z is defined as in b and Y is Cl or Br; and
(d) said phenol has the formula IV or V

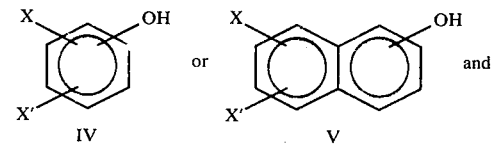

where X and X' are independently selected from the group consisting of -H, Cl-, Br-, F-, alkyl of 1 to 6 carbons, alkoxy of 1 to 6 carbons, aryloxy of 6 to 10 carbons or aryl of 6 to 10 carbons; and when neither X nor X' is hydrogen, X and X' Cannot both be substituted in positions ortho to the hydroxyl group at the same time;
(e) the mole ratio of olefin to hydroperoxide is 0.5:1 to 5:1; and
(f) the t-cumyl halide is charged in an amount of about 5–20 mole percent based on olefin charged.

3. The process of claim 2 wherein the hydroperoxide is selected from cumene hydroperoxide, t-butyl hydroperoxide, t-amyl hydroperoxide, t-hexyl hydroperoxide, 1,1,3,3-tetramethylbutyl hydroperoxide, 2-hydroperoxy-2-methyl-4-hydroxy-pentane, 3-hydroperoxy-3-methylbutyne-1, 2,5-dihydroperoxy-2,5-dimethylhexane, or 2,5-dihydroperoxy-2, 5-dimethylhexyne-3.

4. The process of claim 2 wherein the phenol catalyst is selected from o-cresol, 4-t-butylphenol, 4-chlorophenol, 4-bromophenol, 4-methoxyphenol, beta-naphthol, 2-t-butylphenol, 4-phenylphenol, 3-methoxyphenol or phenol.

5. The process of claim 2 wherein the catalyst is liquified phenol containing about 9% water.

6. The process of claim 2 where the reaction is initiated at 20°–25° C. and the temperature is allowed to rise to 40°–45° C. over ¾–1 hour and the reaction is completed at 40°–45° C.

* * * * *